(12) United States Patent
Babichenko et al.

(10) Patent No.: US 8,404,488 B2
(45) Date of Patent: Mar. 26, 2013

(54) METHOD FOR ON-SITE DRUG DETECTION IN ILLICIT DRUG SAMPLES

(75) Inventors: Sergey Babichenko, Tallinn (EE); Tatjana Ivkina, Apex, NC (US); Larisa Poryvkina, Tallinn (EE); Vitaly Sominsky, Apex, NC (US)

(73) Assignee: Nartest International AS, Tallinn (EE)

( * ) Notice: Subject to any disclaimer, the term of this patent is extended or adjusted under 35 U.S.C. 154(b) by 138 days.

(21) Appl. No.: 12/996,177

(22) PCT Filed: Jul. 7, 2008

(86) PCT No.: PCT/EP2008/058738
§ 371 (c)(1),
(2), (4) Date: Feb. 11, 2011

(87) PCT Pub. No.: WO2010/003447
PCT Pub. Date: Jan. 14, 2010

(65) Prior Publication Data
US 2011/0151570 A1     Jun. 23, 2011

(51) Int. Cl.
*G01N 33/00*    (2006.01)
*G01N 21/64*    (2006.01)

(52) U.S. Cl. ............. 436/93; 436/92; 436/164; 436/171; 436/172; 436/901; 422/82.05; 422/82.08; 356/317

(58) Field of Classification Search .................... 436/92, 436/93, 164, 166, 171, 172, 174, 901; 422/82.05, 422/82.08; 356/317
See application file for complete search history.

(56) References Cited

U.S. PATENT DOCUMENTS
7,995,203 B2 *  8/2011  Babichenko et al. ......... 356/317

FOREIGN PATENT DOCUMENTS
WO        2005111586     * 11/2005

OTHER PUBLICATIONS
Hill et al. Talanta, vol. 76, Apr. 16, 2008, pp. 674-679.*

* cited by examiner

*Primary Examiner* — Maureen Wallenhorst
(74) *Attorney, Agent, or Firm* — Ladas & Parry LLP

(57) ABSTRACT

The invention is provided for detection of Heroin and Morphine in illicit drug samples, also for their differentiation. A liquid sample from a street sample is prepared and divided into two equal aliquots, one of them being reference sample, another being main sample. Both samples are treated with Hydrochloric acid and Sodium hydroxide, but those substances are added to the samples in the different sequence. After that the measurement of SFS of the reference sample is performed. Further the presence of specific spectral pattern of Morphine in the measured SFS of the reference, sample is detected and the value of SFS intensity at the specific spectral point is fixed (a reference value). After 15 minutes for acidification of the main sample, the analogous measurement and detection of the Morphine in the main sample are performed.

7 Claims, 4 Drawing Sheets

Fluorescence of Heroin hydrochloride 3,906-1000 mg/l in water with reagents at 285/340-345 nm before (reagents added in reverse order to prevent hydrolysis) and after conversion to Morphine (due to hydrolysis)

Fluorescence of Morphine sulfate 0,488-2000 mg/l in water with reagents at 285-290/340-345 nm before (reagents added in reverse order to prevent hydrolysis) and after hydrolysis

METHOD FOR ON-SITE DRUG DETECTION IN ILLICIT DRUG SAMPLES

FIELD OF THE INVENTION

The invention relates to the field of drug detection in illicit drug samples. In the sense of the present invention, illicit drug sample is a product that may contain in addition to illicit drug adulterants and/or diluents (also denominated as cutting agents) used for secret substitution of a more expensive illicit drug with cheaper substances or for disguising the existence of an illicit drug. More particularly the invention relates to a method based on fluorescence in solution and specifically on the Spectral Fluorescence Signatures (SFS) technology, allowing detection of Heroin and Morphine and enabling increase of sensitivity of Heroin detection and of selectivity of Heroin and Morphine differentiation in illicit drug samples.

BACKGROUND OF THE INVENTION

A system and a method for on-site drug detection and quantification based on the Spectral Fluorescence Signatures (SFS) technology are disclosed in WO2005111586. The system of this invention consists of an ultraviolet-visible light source, a condenser/filter assembly with filter drive, an excitation monochromator with diffraction grating drive, a reference photo-detector, a cell assembly for liquid, solid and powder samples, an absorption photo-detector, an emission monochromator with diffraction grating drive, and an emission photo-detector. A microcontroller unit is provided for device controlling, data processing, and communication with an external computer via different link types. The detection and quantification of illicit drugs in the analyzed sample are provided by measuring simultaneously the emission spectra of fluorescence at every step of excitation wavelength in selected and fixed excitation, emission and absorption spectral windows in a way to cover specific excitation, emission fluorescence and absorption spectral ranges of all major drugs, adulterants and diluents; and processing the united result in a computer system based on combination of preliminary prepared spectral library and specialized software consisting of identification, interaction verification and automatic calibration modules.

A system and a method of analysis of illicit drug samples disclosed in WO2005111586 are limited in detection by the concentration of the substances of interest, in particular Heroin. Due to low fluorescence efficiency of Heroin and interfering influence of adulterants and diluents, the specific patterns in SFS structure caused by said substances at certain concentration of Heroin are not recognized by the expert system.

WO 2008040386 discloses a method for on-site drug detection in illicit drug samples enabling preferably Cocaine drug detection in street samples containing in addition to Cocaine also adulterants and/or diluents. The method provides preparing of the liquid street sample, taking of an aliquot of said sample, its analysis with help of SFS (Spectral Fluorescence Signatures) technology, fixing the result of analysis as a reference value, the subsequent acidification of the liquid sample, taking an aliquot of the acidified liquid sample and its analysis with help of SFS technology, fixing the result of analysis and comparing said result with the reference value. The result of comparison enables to differentiate between Cocaine Base and Cocaine hydrochloride in the street sample. On the essence, the subject invention uses an additional chemical reaction for modifying the sample before performing the second measurement. This chemical reaction enables to raise the intensity of the sample for analysis with SFS technology by way of converting Cocaine Base to Cocaine hydrochloride.

The above method as such cannot be used for detection of Heroin in illicit drug samples because the simple acidification of a sample and comparison the results of the measurement of the sample before and after acidification does not grant the reliable results due to the specific chemical qualities of Heroin and existence of adulterants and/or diluents in the sample.

At the same time, the need for a technical solution, which increases the sensitivity and selectivity of on-site analysis related to Heroin and Morphine detection in a mixture with cutting agents (adulterants and diluents) is mandated by the legal requirements in illicit drug distribution prevention. The current sentencing structure for Heroin offences (United States Sentencing Commission. Guidelines Manual. 2006) in the Schedule I of the referenced document provides for the less than 5 g of Heroin the same sentences as for about 25 g of Cocaine. Liability for seized 1 g of Heroin is equal according to this document to 1 kg of Marijuana (Marihuana). Sentencing structure for Morphine offences has been put in the Schedule II. Liability for seized 1 g of Morphine is equal according to the same document to 500 g of Marijuana (Marihuana). The cited documents illustrate necessity to provide reliable and selective detection of Heroin and Morphine to fight effectively against this illegal drugs trafficking and abuse.

SUMMARY OF INVENTION

Resulting from the drawbacks of the known technical solutions, the first objective of the present invention is to provide a method for on-site drug detection in illicit drug samples using SFS analysis enabling reliable detection of Heroin and Morphine in a sample.

Another objective of the present invention is to increase the sensitivity and selectivity of SFS analysis for Heroin detection in the mixtures with cutting agents.

Further objective of the present invention is to ensure the safe differentiation of Heroine and Morphine in a sample. To solve the problem of detection limits due to low fluorescence efficiency of Heroin and interfering influence of adulterants and diluents, a chemical conversion of Heroin to Morphine suitable for on-site use was elaborated by the inventors. Morphine has higher fluorescence efficiency than Heroin, its spectral patterns in SFS structure are different by shape and position compared to Heroin, and therefore the presence of Morphine in converted sample can serve as a good indicator of Heroin presence in initial sample. Conversion of Heroin to Morphine in alkali has been applied.

According to this procedure false positive detection of Heroin may occur if Morphine is present in drug sample as an independent component or as a result of partial Heroin self-conversion. Therefore differentiation of Heroin in presence of Morphine and exclusion of false positive results in drug sample is required. It is provided by detection of Morphine presence in drug sample before applying the procedure of chemical conversion to the sample.

For achieving the above objectives, the suggested method for on-site drug detection in illicit drug samples is based on the analysis by Spectral Fluorescence Signatures (SFS) technology and is provided by executing the following steps: preparing a liquid sample from of a street sample for analysis;

allotting the liquid sample into two equal aliquot samples, first of which is the reference sample and the second one is the main sample;

prior to the measurement, first the Hydrochloric acid and then Sodium hydroxide are added into the reference sample;

the reference sample is introduced in the into the measuring cell of a SFS device;

the measurement of SFS of the reference sample is performed;

the presence of specific spectral pattern of Morphine in the measured SFS of the reference sample is detected and the value of SFS intensity at the specific spectral point is fixed;

the value of SFS intensity of the reference sample at the specific spectral point is considered as a reference value;

prior to the measurement, Sodium hydroxide is added to the main sample;

after expiring the time limit provided for hydrolysis of the main sample, Hydrochloric acid is added to the sample in order to stop the hydrolysis process;

the main sample is introduced in the into the measuring cell of a SFS device;

the measurement of SFS of the main sample is performed;

the presence of specific spectral pattern of Morphine in the measured SFS of the main sample is detected and the value of SFS intensity at the specific spectral point is fixed;

the reference value and the value of SFS intensity of the main sample at the specific spectral point are compared, and, if the reference value and the value of SFS intensity of the main sample at the specific spectral point both equal zero, existence neither Heroin nor Morphine in the street sample is considered proved;

if the reference value differs from zero, the existence of Morphine in the street sample is considered proved;

if the value of SFS intensity of the main sample at the specific spectral point equals to the reference value lacking of Heroin in the street sample is considered proved;

if the value of SFS intensity of the main sample at the specific spectral point exceeds the reference value, the existence of Heroin in the street sample is considered proved.

The SFS specific spectral point for comparison is 285/345 nm

The preferred time limit provided for conversion of Heroin to Morphine is 15 minutes.

DETAILED DESCRIPTION OF THE INVENTION

According to the present invention, the first step of the method is preparing the liquid sample for analysis. For this purpose the sampled amount of dry sample as a powder taken by a sampling tool (e.g. spatula) is transferred into purified water, and water with powder is mixed to assist dilution of the powder in water. Usually 20 mg of a powder is diluted in 10 ml of purified water but it has been revealed that the amount of the power may vary from 18 to 23 mg, this variation does not influence the results of the further measurements.

Figure 4:
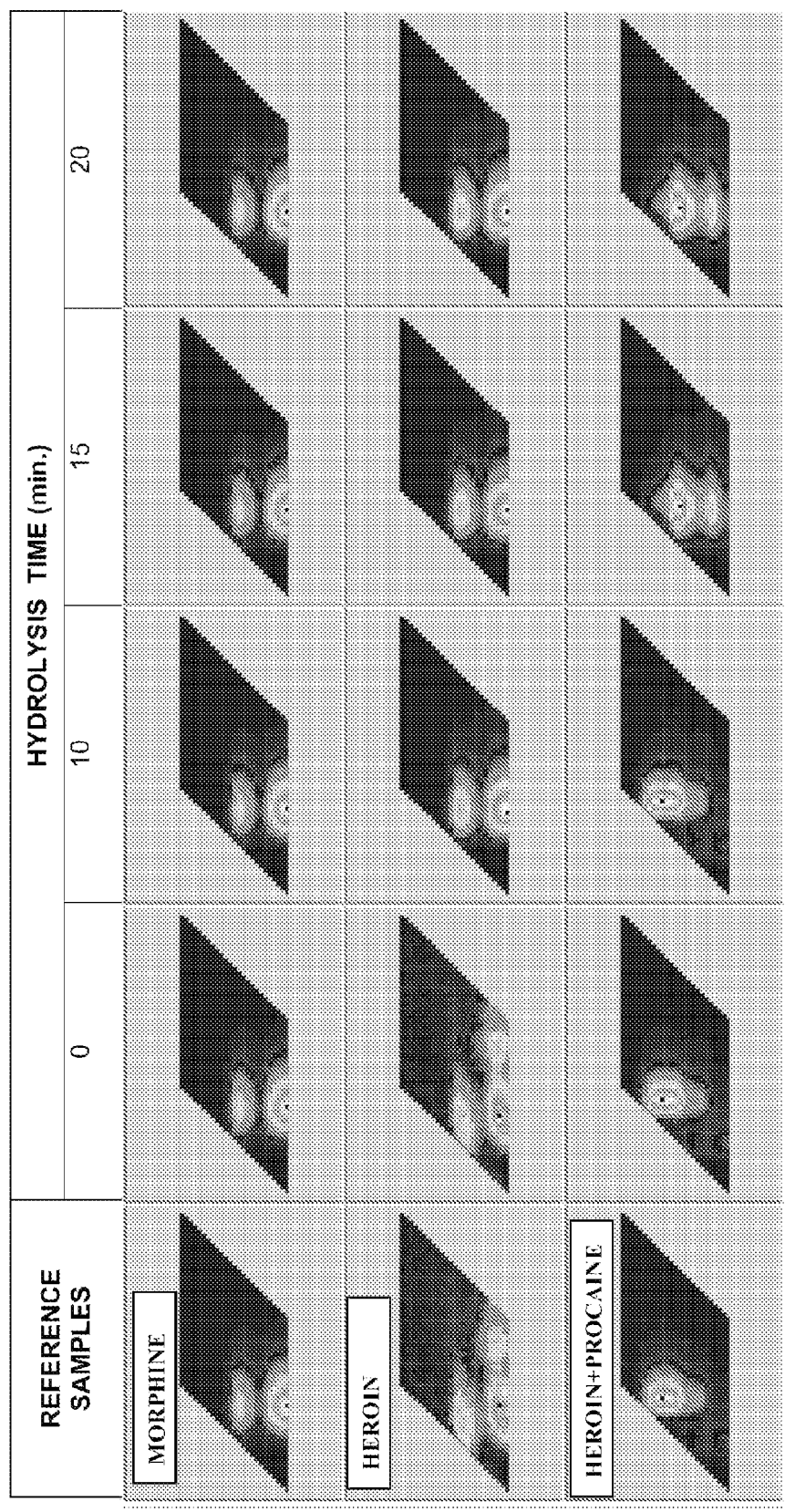
FIG. 4. Spectral Fluorescence Signatures of Morphine, Heroin, and Heroin in the mixture with Procaine before (reference samples) and in the process of conversion (hydrolysis).

After that, the liquid sample is divided into 2 equal aliquots—the reference sample and the main one. Sodium hydroxide is added to the main sample in order to convert possibly present Heroin to Morphine by way of hydrolysis process. The amount of the added Sodium hydroxide is 3-5 drops. Conversion is stopped after 15 minutes by addition of 3-5 drops of Hydrochloric acid The time of the conversion is substantiated by the experiments performed by the inventors—with reference to FIG. 4 it is evident that after passing of 15 minutes hydrolysis of the main sample, the Spectral Fluorescence Signature of Heroin has been transferred to the SFS of Morphine. Even by the presence of cutting agents in the sample (e.g. Procaine as one of the wide-spread cutting agent in the sized Heroin samples) the above time-limit is sufficient to reach the SFS of the sample very near to the SFS of Morphine and acceptable for the SFS measurement. Thus the time-limit found by the inventors is sufficient to provide Heroin detection in different mixtures.

To the reference sample, 3-5 drops of Hydrochloric acid is added to prevent conversion of possibly present Heroin, and 3-5 drops of Sodium hydroxide after it to keep contents of two aliquots the same. Affecting the reference sample with the chemical substances mentioned above is necessary for achieving the more reliable results of measurement—due to the possible existence adulterants and diluents in the street sample, the both samples to be measured have to be affected by the identical additional chemicals in order to prevent the possible distortions which may arise when only the main sample is additionally processed with Sodium hydroxide and Hydrochloric acid, The reference sample is introduced into the measurement cell of the device according to WO2005111586 and SFS of the aliquot of liquid sample is measured. Upon acquisition of the SFS, the expert system of the device based on the spectral patterns recognition in measured SFS provides detection of Morphine in the sample, and registers the intensity value at the specific point (285/345 nm) if Morphine detected.

The procedure of Heroin conversion for on-site use must be simple and fast. There are at least two methods of Heroin conversion into Morphine: acid and alkali hydrolysis. The experiments completed by inventors have revealed that the acid hydrolysis [D. Zhang et al] requires heating of the sample for efficient conversion in enough short time. As heating complicates the realization of procedure on-site, this method has been rejected. Alkali hydrolysis using Sodium hydroxide [G. Nakamura] has been tested and accepted as enough efficient and simple method of Heroin conversion to Morphine. Sodium hydroxide concentration influences speed of hydrolysis but should be as low as possible for on-site use because lower concentration decreases potential risk for performers of the process. Sodium hydroxide in the cited works has been used in 2N or 1N concentrations but the inventors have determined that 0.5N is enough to provide conversion of Heroin into Morphine within acceptable time interval for on-site use.

After possibly present Heroin has passed the established time for conversion into Morphine, and the Hydrochloric acid is added to the sample to stop the further conversion, the main sample is introduced into the measurement cell of the device, and the SFS of the sample is measured. Upon acquisition of the SFS, the expert system of the device provides the detection of Morphine in the sample, registers the intensity value at the specific point of the SFS if Morphine detected, and compares the intensity value with that of the reference sample.

Figure 1:
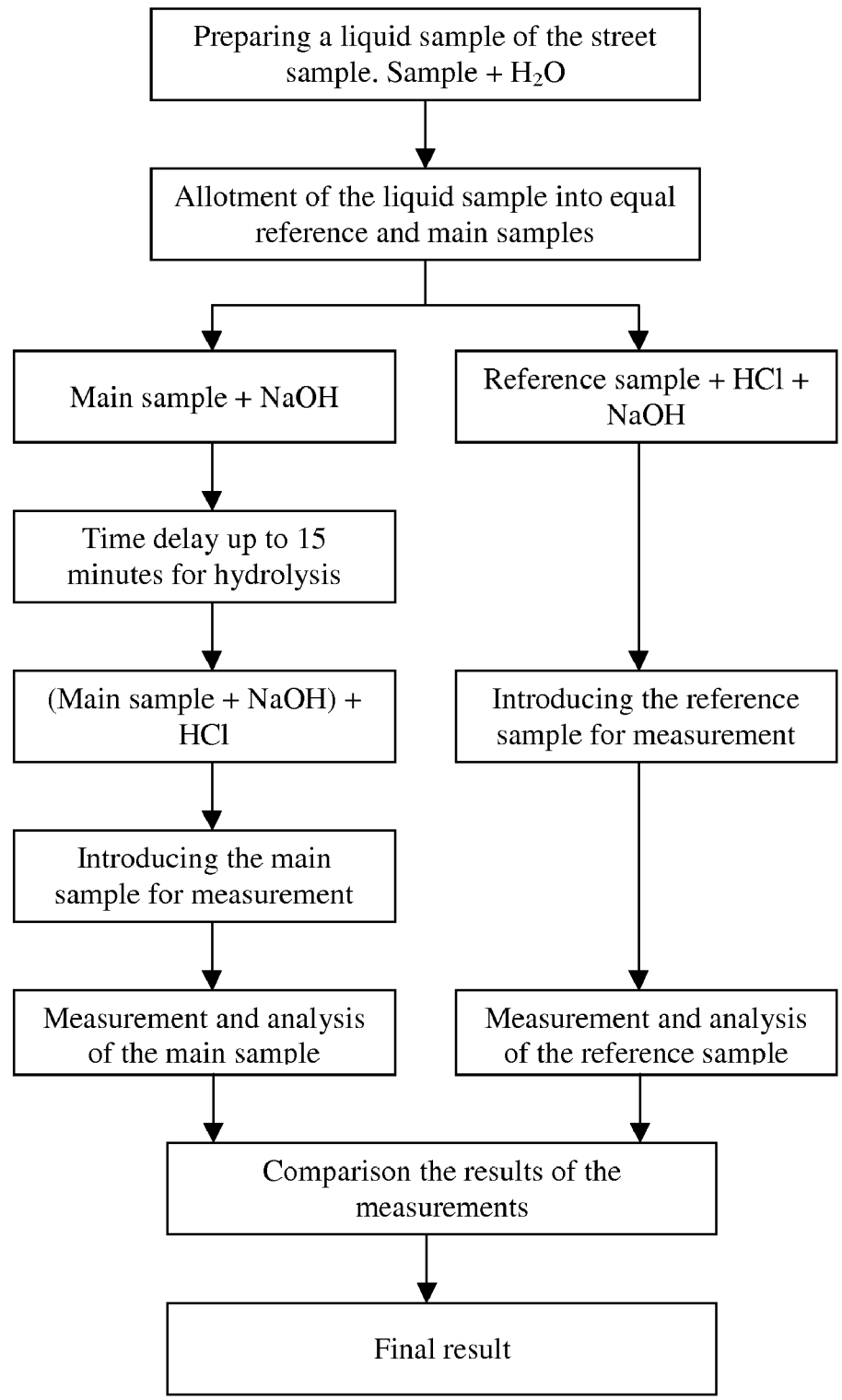
FIG. 1. The flow-chart of the method for detection of Heroin and Morphine in the illicit drug samples FIG. 2. Intensity of Heroin hydrochloride fluorescence at the specific point 285/340-345 nm in the concentration range of 3.9-1000 mg/l in water with reagents before (reagents added in the reverse order to prevent hydrolysis) and after conversion to Morphine (due to hydrolysis)—the results of measurement of the reference sample and the main one.
Figure 2:
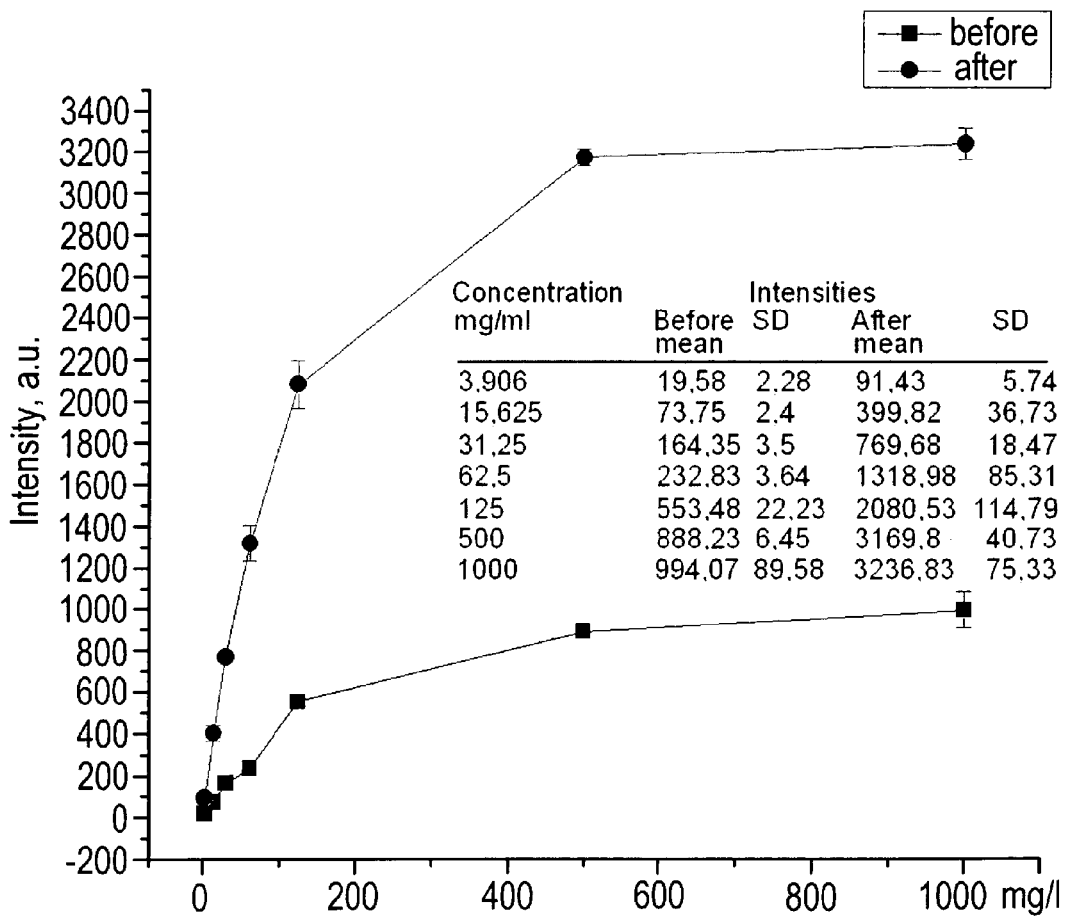
Figure 3:
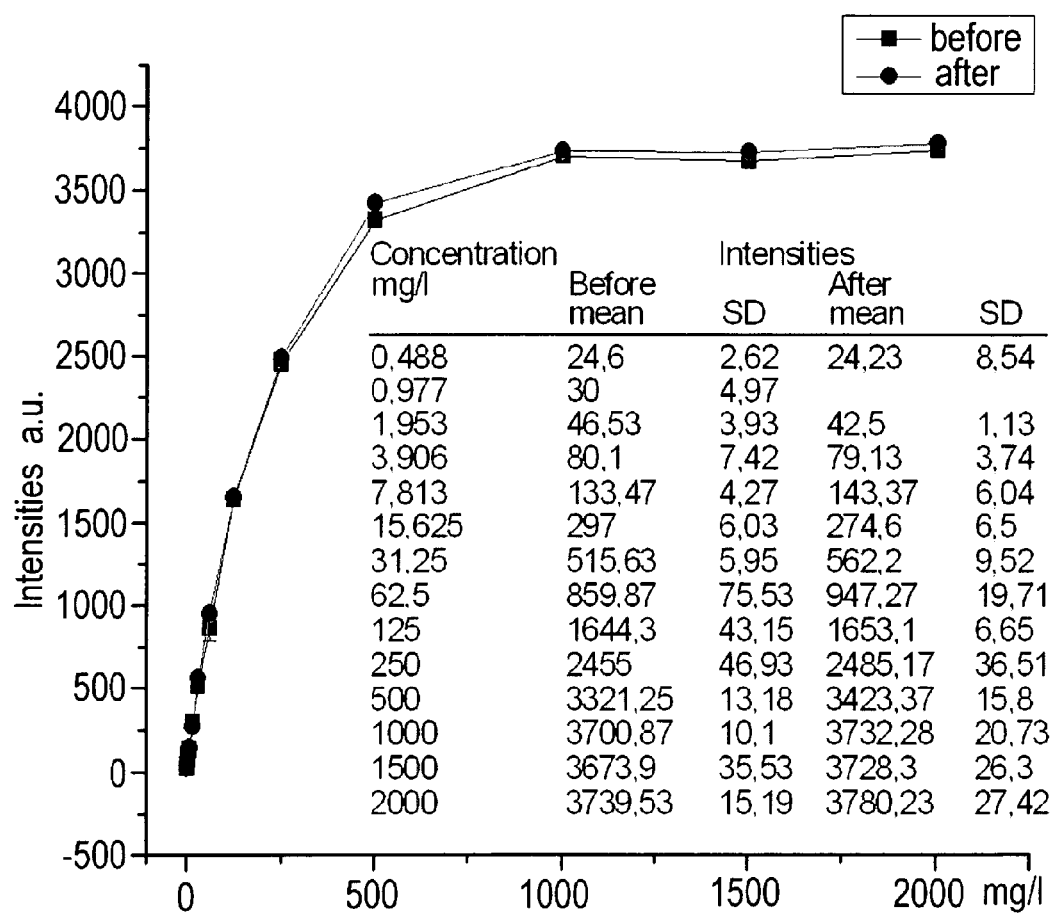
FIG. 3. Intensity of Morphine sulphate fluorescence at the specific point 285/340-345 nm in the concentration range of 0.488-2000 mg/l in water with reagents before (reagents added in the reverse order to prevent hydrolysis) and after hydrolysis—the results of measurement of the reference sample and the main one.

Presence of Morphine in the reference sample may be due to a spontaneous hydrolysis of Heroin in the seized sample before analysis. Morphine may also be present independently on Heroin. If Morphine is detected in the reference sample and in the main sample after hydrolysis, and the fluorescence intensity at the specific point of SFS is increased, it is evidence of Heroin presence in the analyzed sample (FIG. 2). There is no other source of such result because fluorescence of Morphine is not increased after hydrolysis (FIG. 3). Only increase of Morphine concentration due to conversion from Heroin may be the origin of SFS intensity rise in the described procedure.

Accordingly, absence of Morphine in the reference sample and its presence in the main sample after hydrolysis is the evidence of Heroin presence in the analyzed drug sample.

If Morphine is detected in the reference sample and in the main sample after hydrolysis but the fluorescence intensity of the main sample at the specific point of SFS is not increased, it is evidence of Morphine presence and absence of Heroin in the analyzed drug sample.

A step-by-step performance of the present invention is shown below.
1. Transferring a proper amount of drug sample into a test container with a rational volume of pure water.
2. Giving the amount of drug sample to be dissolved at possible instant within 3 minute time interval and allowing any insoluble materials settle to the bottom of the container.
3. Division of the liquid sample for two equal samples (reference sample and main one).
4. Addition of Hydrochloric acid to the reference sample
5. Addition of Sodium hydroxide to both samples
6. Leaving the main sample for 15 minutes (hydrolysis for converting of Heroin to Morphine)
7. Taking a proper volume of the liquid from the reference sample and placing it into the measurement cell of the SFS measuring device according to WO2005111586.
8. Measuring the SFS of the reference sample and detecting spectral pattern of Morphine if present. The result of the measurement of the intensity of Morphine fluorescence at the specific point of SFS serves as the reference value.
9. After passing of 15 minutes, adding Hydrochloric acid to the main sample for stopping the hydrolysis process.
10. Taking a proper volume of the liquid from the main sample and placing it into the measurement cell of the SFS measuring device according to WO2005111586.
11. Measuring the SFS of the main sample and detecting specific spectral pattern of Morphine if present. The result of the measurement of the intensity of Morphine fluorescence at the specific point of SFS of the main sample will be compared with the reference value,
12. Comparing the intensities of Morphine fluorescence of the reference and main samples provided that the intensity of Morphine fluorescence of the reference sample is detected. Higher intensity of the fluorescence of the main sample indicates that Heroin is present in analyzed drug sample. And on the contrary, lower or unchanged intensity of the fluorescence of the main sample indicates that only Morphine is present in analyzed drug sample. Absence of Morphine in the reference sample and its appearance in the main sample is evidence of Heroin presented in analyzed drug sample. Absence of Morphine fluorescence in the both samples indicates that neither Morphine nor Heroin are present in analyzed drug sample.

The table below illustrates the results of detection of Heroin in street samples according to the present invention. As in the street samples ##2, 3 and 15 the difference between the reference value and the result of the measurement of SFS of the main sample in the SFS specific spectral point is unessential, it may be concluded that those street samples do not contain Heroin. For all the remaining street samples the adversative conclusion can be made.

| Street sample # | Morphine detected before hydrolysis Intensity (a.u.) at 285/345 nm | Morphine detected after hydrolysis Intensity (a.u.) at 285/345 nm | Increase of intensity, % |
| --- | --- | --- | --- |
| 1 | 75.5 | 209.8 | +173 |
| 2 | 1094.0 | 1275.7 | +21 |
| 3 | 1643.5 | 2534.8 | +54 |
| 4 | 718.3 | 2447.4 | +241 |
| 5 | 140.0 | 1279.0 | +814 |
| 6 | 436.0 | 2242.9 | +414 |
| 7 | 499.4 | 2890.2 | +479 |
| 8 | 297.3 | 2849.0 | +858 |
| 9 | 1110.3 | 2431.3 | +119 |
| 10 | 457.4 | 2441.6 | +478 |
| 11 | 364.7 | 2981.0 | +704 |
| 12 | 272.0 | 2727.8 | +903 |
| 13 | 308.2 | 3485.4 | +1031 |
| 14 | 447.9 | 2871.9 | +542 |
| 15 | 497 | 836 | +48 |
| 16 | 440.1 | 2904.3 | +560 |

The procedure of Heroin detection can be provided automatically by Expert system analyzing the SFS. Such expert system considers not only the shape and position of Morphine spectra but their intensities and appearance of Morphine spectral pattern or increase of its fluorescence intensity.

The disclosed embodiment of the invention does not determine its scope of protection, but shows only one of variants of its realization within the scope defined by claims.

References

WO2005111586. S. Babichenko, E. Erme, T. Ivkina, L. Poryvkina, V. Sominsky. A PORTABLE DEVICE AND METHOD FOR ON-SITE DETECTION AND QUANTIFICATION OF DRUGS.

WO2008040386. S. Babihenko, T. Ivkina, L. Poryvkina, V. Sominsky. METHOD FOR ON-SITE DRUG DETECTION IN ILLICIT DRUG SAMPLES.

D. Zhang et al. Origin differentiation of Heroin sample and its acetylating agent $^{13}C$ isotope ratio mass spectrometry. Eur. J. Mass Spectrom. 11, 277-285 (2005).

G. Nakamura, T. Ukita. Codeine to Morphine Ratio of Illicit Heroin Hydrolysates. UNODC—Bulletin on Narcotics, 1963,1-008; G. Nakamura and J. Thornton. KINETICS OF HEROIN DEACETYLATION IN AQUEOUS ALCALINE SOLUTION AND IN HUMAN SERUM AND WHOLE BLOOD. Journal of Chromatography, 110: 81-89 (1975).

The invention claimed is:

1. A method for on-site drug detection of an illicit drug sample, comprising the steps of:
   (i) preparing a liquid sample from a dry sample of the illicit drug sample by dissolving said dry sample in purified water;
   (ii) dividing the liquid sample into two portions comprising a reference sample and a main sample;

(iii) adding hydrochloric acid and then sodium hydroxide into the reference sample;

(iv) measuring Spectral Fluorescence Signatures ("SFS") of the reference sample in order to detect the presence of a spectral pattern of morphine at a selected spectral point of SFS having the excitation wavelength 285 nm and emission wavelength of 340-345 nm wherein the measured SFS of the reference sample serves as a first reference value;

(v) adding sodium hydroxide to the main sample to convert heroin into morphine through hydrolysis, and allowing a sufficient rest period for hydrolysis;

(vi) adding hydrochloric acid to the main sample in order to stop the hydrolysis process;

(vii) measuring SFS of the main sample at the selected spectral point of SFS in order to detect the presence of spectral pattern of morphine;

(viii) comparing the first reference value with the value of SFS intensity of the main sample at the selected spectral point of SFS.

2. Method for on-site drug detection of an illicit drug sample according to claim 1, wherein, if the comparison reveals the first reference value and the value of SFS intensity of the main sample at the selected spectral point of SFS are both equal to zero, the conclusion is made that neither heroin nor morphine are present in the illicit drug sample.

3. Method for on-site drug detection of an illicit drug sample according to claim 1, wherein, if the comparison reveals the first reference value differing from zero, the conclusion is made that morphine is present in the illicit drug sample.

4. Method for on-site drug detection of an illicit drug sample according to claim 1, wherein, if the comparison reveals the first reference value being equal to the value of SFS intensity of the main sample at the selected spectral point of SFS, the conclusion is made that no heroin is present in the illicit drug sample.

5. Method for on-site drug detection of an illicit drug sample according to claim 1, wherein, if the result of the comparison reveals the value of SFS intensity of the main sample at the selected spectral point of SFS is greater than the first reference value, the conclusion is made that heroin is present in the illicit drug sample.

6. Method for on-site drug detection of an illicit drug sample according to claim 1, wherein distilled water is used as purified water.

7. Method for on-site drug detection of an illicit drug sample according to claim 1, wherein the rest period for hydrolysis of the main sample is up to 15 minutes.

\* \* \* \* \*